United States Patent [19]

Sattler

[11] Patent Number: 5,739,399
[45] Date of Patent: Apr. 14, 1998

[54] PROCESS FOR THE PREPARATION OF CYCLOPROPANECARBOXYLIC ACID AMIDES

[75] Inventor: Andreas Sattler, Düsseldorf, Germany

[73] Assignee: Bayer Aktiengesellschaft, Leverkusen, Germany

[21] Appl. No.: 763,776

[22] Filed: Dec. 11, 1996

[30] Foreign Application Priority Data

Dec. 20, 1995 [DE] Germany ............... 195 47 635.2

[51] Int. Cl.$^6$ .................................. C07C 231/02
[52] U.S. Cl. ............................. 564/138; 564/190
[58] Field of Search ........................... 564/138, 190

[56] References Cited

U.S. PATENT DOCUMENTS

| | | | |
|---|---|---|---|
| 4,379,928 | 4/1983 | Theodoropulos | 544/176 |
| 4,670,444 | 6/1987 | Grohe et al. | |
| 5,068,428 | 11/1991 | Diehl et al. | 564/134 |
| 5,364,966 | 11/1994 | Kisida et al. | 564/190 |

FOREIGN PATENT DOCUMENTS

| | | |
|---|---|---|
| 1171098 | 7/1984 | Canada . |
| 43949 | 1/1982 | European Pat. Off. . |
| 0 365 970 A2 | 5/1990 | European Pat. Off. . |
| 0 662 470 | 7/1995 | European Pat. Off. . |
| 0 662 470 A1 | 7/1995 | European Pat. Off. . |
| 0 662 470 B1 | 7/1995 | European Pat. Off. . |
| 31 42 854 A1 | 5/1983 | Germany . |
| WO94/15905 | 7/1994 | WIPO . |

OTHER PUBLICATIONS

Mazur et al., "Small–ring Compounds, etc.," Journal of the American Chemical Society, vol. 81, pp. 4390–4398, Aug. 1959.
N. Kishner, Chem.Zentralblatt I, 1703–1704 (1905).
Paul Dalle, Chem.Zentralblatt I, 913–914 (1902).
Derwent Database, a.n. 74–67216V, abstract of JP 49-31, 977 (1974).

Primary Examiner—Peter O'Sullivan
Attorney, Agent, or Firm—Sprung Kramer Schaefer & Briscoe

[57] ABSTRACT

Cyclopropanecarboxylic acid amides

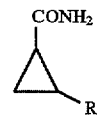

wherein
R represents hydrogen, straight-chain or branched $C_1$–$C_4$-Alkyl, optionally substituted aryl or optionally substituted aralkyl,
can be prepared directly from the corresponding cyclopropanecarboxylic acid by reaction with ammonia under pressure in a suitable organic solvent.

12 Claims, No Drawings

PROCESS FOR THE PREPARATION OF CYCLOPROPANECARBOXYLIC ACID AMIDES

Cyclopropanecarboxylic acid amides are important organic intermediates, such as, at example, cyclopropanecarboxylic acid amide itself which, as a precursor, for example after conversion to cyctopropylamine, represents a significant component for the synthesis of important active compounds in the pharmaceutical and plant protection sectors (for example: DE-A 3 142 854). Such a use requires preparation processes for the intermediates, which give the product not only in a relatively high purity and high yield but, furthermore, in order to avoid impurities, contribute to high economic efficiency by the use of as few reagents as possible and by the most direct synthesis possible, without intermediate stages.

Some preparation processes for cyclopropanecarboxylic acid amides are already known; all of these, however, start from derivatives of the underlying cyclopropanecarboxylic acid and additionally require catalysts. Thus, in EP-A 0 365 970, $C_4$–$C_8$-alkyl esters of cyclopropanecarboxylic acid, such as for example, the isobutyl ester, are reacted with a 35% strength melt of sodium isobutanolateisobutanol as catalyst and ammonia at about 6 bar and 100° C. to give the amide. This gives the cyclopropanecarboxylic acid amide in a yield of about 88%. Due to the isobutanol released during the reaction, the reaction mixture obtained after the reaction can be stirred and can readily be filtered. The process is applicable only to esters of cyclopropanecarboxylic acid and, furthermore, only to higher alkyl esters. Moreover, butylate as a catalyst in quantities of around 10 Mol-% to 20 Mol-% is always required before successfully amidating the esters. In EP 0 662 470, a very similar process for $C_1$–$C_3$-alkyl esters of cyclopropanecarboxylic acid is described, wherein, for example, the methyl ester is reacted with a 30% strength solution of sodium methylate/methanol as catalyst and ammonia at about 1 to 3 bar and 60° to 100° C. to give the amide. After the methanol has been distilled off, this gives the cyclopropanecarboxylic acid amide in a yield from 85 to 90%. By stopping the reaction in good time at a conversion of about 80%, the reaction mixture obtained in this case after the reaction is maintained stirrable and readily filterable. This process, again, requires esters as reactants, and here again a catalyst (methylate) is required in a not inconsiderable quantity of 10 Mol-% to 30 Mol-% for successfully amidating the esters. Both processes thus give cyclopropanecarboxylic acid amide admittedly in high yields and high purity, but they are restricted to esters as reactive derivatives of cyclopropanecarboxylic acid and, furthermore, require not inconsiderable quantities of catalysts and involve in some cases making-up procedures which require distillations and filtrations.

Direct reactions of the cyclopropanecarboxylic acid chlorides with ammonia in basic solvents, with elimination of hydrochloric acid, have been known for a long time in the literature (Dalle, Centralblatt 1902 I, 913/Kishner, Centralblatt 1905 I, 1704/Mazur et al., J. Am. Chem. Soc 1959, 81, 4390). However, the carboxylic acid chlorides are as a rule initially obtained from the carboxylic acids by reaction with thionyl chloride or phosgene. The reaction of the acid chlorides requires auxiliary bases or at least twice the molar quantifies of ammonia. Another disadvantage of these processes frequently is the formation of large salt residues as a result of the neutralization reaction.

For just a few substituted cyclopropanecarboxylic acid amides, preparation processes such as those presented above for cyclopropanecarboxylic acid amide have also been described.

So far, no process for the direct amidation of cyclopropanecarboxylic acid or substituted cyclopropanecarboxylic acids with ammonia is known, either with or without the use of catalysts.

It was thus the object of the invention to obtain cyclopropanecarboxylic acid amide not via a more reactive intermediate stage such as an ester or an acid chloride, but directly from the cyclopropanecarboxylic acid by amidation with ammonia in high yields, in order to achieve optimum space/time yields. In this case, no catalysts should have to be used, a high purity of the product should be achieved and the amidation should be run under pressure and temperature conditions which do not conflict with industrial feasibility. Such a process would be highly efficient and, especially in economic respects, far superior to the existing processes.

Surprisingly, a process for the preparation of cyclopropanecarboxylic acid amides has now been found which, starting directly from the corresponding cyclopropanecarboxylic acids, gives the desired compounds in high purity and with very good space/time yields. An activation of the cyclopropanecarboxylic acids by derivatizing to the ester or acid chloride is not necessary.

The present invention relates to a process for the preparation of cyclopropanecarboxylic acid amides of the general formula

wherein

R represents hydrogen, straight-chain or branched $C_1$–$C_4$-Alkyl, optionally substituted aryl or optionally substituted aralkyl, by reacting the corresponding cyclopropanecarboxylic acid with ammonia at a pressure of 1 to 300 bar in the presence of an organic solvent.

Possible substituents for the optionally substituted aryl radicals and aralkyl radicals in the definition of R are especially halogen, such as fluorine, chlorine and bromine, and also nitro, cyano, COOH and $COOC_1$–$C_4$-Alkyl.

Aryl radicals are to be understood especially as phenyl and naphthyl, and aralkyl preferably represents phenyl-$C_1$–$C_4$-Alkyl or naphthyl-$C_1$–$C_4$-alkyl, especially benzyl.

The cyclopropanecarboxylic acid amide, which has precipitated after the reaction, can be isolated very simply in high yields by filtration. The reaction mixture obtained after the reaction is stirrable, and a simple filtration represents the entire working-up. With a procedure in accordance with the process of the invention, yield losses as in the ester amidation according to the EP 0 662 470 or the unavoidable presence of certain alcohols, being formed during the ester amidation, as additives, as in EP-A 0 365 970 do not occur. The space/time yield is markedly higher than in the alternative processes mentioned, since only water and no higher-molecular alcohols or HCl are eliminated in the reaction of the substrate to give the cyclopropanecarboxylic acid amide.

The process according to the invention is preferably carried out in the absence of catalysts. In certain cases, however, the use of a catalyst can be of advantage. Possible dehydration catalysts in this case are in particular: salts of alkali metals and alkaline earth metals with inorganic acids, such as, for example, magnesium sulfate, sodium sulfate, magnesium chloride, calcium chloride, calcium carbonate or alternatively alkali metal borates and alkaline earth metal borates, and also oxides of metals of the main groups and subgroups, such as, for example, aluminum oxide, titanium dioxide or zirconium oxide, as well as organic phosphorous acid derivatives such as, for example, triethyl phosphite.

If a catalyst is added to the reaction mixture, this is preferably done in quantities from 5 Mol-% to 100 Mol-%, relative to the optionally substituted cyclopropanecarboxylic acid.

To carry out the process according to the invention, almost all common, inert organic solvents or mixtures thereof can be used, such as, say, aromatic or aliphatic hydrocarbons which can also be halogenated, such as, for example, xylenes, toluene, benzene, alkylaromatics, tetralin, ligroin, petroleum ether, chlorobenzene, methylene chloride, chloroform, ethers such as, for example, diethyl ether, dibutyl ether or THF, and polar aprotic solvents such as, for example, DMF, DMSO, sulfolan or N-methylpyrrolidone, and preferably xylenes, toluene, THF, DMF or DMSO are employed, and particularly preferably xylenes or toluene are used.

In general, solutions containing 5–80% by weight of optionally substituted cyclopropanecarboxylic acid are amidated, preferably solutions containing 30–60% by weight and very particularly preferably containing 40–50% by weight.

The process according to the invention can be carried out within a very wide ammonia pressure range from, for example, 1 to 300 bar. In general, ammonia pressures of 1–50 bar, preferably of 10–30 bar and very particularly preferably of only 15–20 bar are used.

The amidation is in general carried out in a temperature range from 50° C. to 300° C., and a range between 100° C. and 200° C., particularly preferably between 160° C. and 190° C., is preferred.

Furthermore, a particular advantage of the process according to the invention is a reaction time which is short under the mild pressure and temperature conditions indicated as being preferred, and which amounts to, for example, between 3 and 24 hours, or preferably between 6 and 12 hours.

A further advantage of the process according to the invention is that the amide can easily be isolated by filtration from the stirrable suspension formed after the reaction, and even in spite of almost complete conversion.

When the process according to the invention is carried out, the procedure is in general such that the optionally substituted cyclopropanecarboxylic acid is first introduced together with the solvent or the solvent mixture into an autoclave, if appropriate with addition of a catalyst, and ammonia is then injected under control at room temperature, after the autoclave has been sealed. The latter is then heated to the desired reaction temperature, the working pressure being established which is preferably maintained within the first hours of the reaction time by the addition of small quantities of ammonia. After completion of the reaction, the autoclave is cooled and let down, and the amide is isolated by filtration.

The process according to the invention is illustrated in more detail in the examples which follow.

EXAMPLE 1

Cyclopropanecarboxylic acid amide p 108.6 g of 95% pure cyclopropanecarboxylic acid (1.2 mol) in 150 ml of xylene are first introduced into a 0.7 l autoclave. 65 ml of ammonia are added and the mixture is then heated to 180° C., an internal pressure of 20.5 bar being established. After one hour at the above temperature, the pressure has fallen to 19 bar, and another 5 ml of NH$_3$ are added. After a further hour, again a further 7 ml of ammonia are added, and stirring is continued for ten hours at 180° C. and 20 bar. The mixture is allowed to cool and the autoclave is let down. The readily stirrable suspension is taken out, the cyclopropanecarboxylic acid amide which has precipitated is filtered off with suction and rinsed with 20 ml of xylene. After drying of the product in vacuo at 70° C., this gives 92.8 g of cyclopropanecarboxylic acid amide in a purity of 96.5%.

EXAMPLE 2 cis/trans-2-Methylcyclopropanecarboxylic acid amide 15 g of 98% pure cis/trans-2-methylcyclopropanecarboxylic acid (0.147 mol) in 15 ml of xylene are first introduced into a 50 ml autoclave. 10 ml of ammonia are added, and the mixture is then heated to 180° C., an internal pressure of 20 bar being established. After one hour at the above temperature, the pressure has fallen to 19.3 bar, and a further 5 ml of NH$_3$ are added, and stirring is then continued for 10 hours at 180° C. and 20 bar. The mixture is allowed to cool and the autoclave is let down. The readily stirrable suspension is taken out, the cis/trans-2-methylcyclopropanecarboxylic acid amide which has precipitated is filtered off with suction and rinsed with 10 ml of xylene. After drying of the product in vacuum at 70° C., this gives 11.1 g of cis/trans-2-methylcyclopropanecarboxylic acid amide (0.112 mol).

What is claimed is:

1. A process for the preparation of cyclopropanecarboxylic acid amides of the general formula

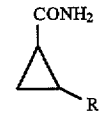

wherein

R represents hydrogen, straight-chain or branched $C_{1-C4}$-alkyl, optionally substituted aryl or optionally substituted aralkyl, which comprises reacting the corresponding cyclopropanecarboxylic acid with ammonia at ammonia pressures of 1 to 300 bar in the presence of an organic solvent to give the amide.

2. The process as claimed in claim 1, which is carried out in the absence of a catalyst.

3. The process as claimed in claim 1, wherein at least one solvent from the group comprising aromatic and aliphatic hydrocarbons esters and polar aprotic solvents is used as the organic solvent.

4. The process as claimed in claim 1, wherein the solvent is a halogenated aromatic or aliphatic hydrocarbon.

5. The process as claimed in claim 1, wherein xylenes or toluene or any desired mixture of these solvents is used as the solvent.

6. The process as claimed in claim 1, wherein solutions of the corresponding cyclopropanecarboxylic acid in the organic solvent containing 5–80% by weight are reacted with ammonia.

7. The process as claimed in claim 1, which is carried out at ammonia pressures of 1–50 bar.

8. The process as claimed in claim 1, wherein the reaction with ammonia is carried out in a temperature range from 50° C. to 300° C.

9. The process as claimed in claim 1, wherein the amide is isolated by filtration.

10. The process according to claim 1, wherein no catalyst is used.

11. The process according to claim 1, wherein a dehydration catalyst is used.

12. The process according to claim 11, wherein the dehydration catalyst is magnesium sulfate, sodium sulfate, magnesium chloride, calcium chloride, calcium carbonate, an alkali metal borate, a alkaline earth metal borate, aluminum oxide, titanium dioxide, zirconium oxide or triethylphosphite.

* * * * *